United States Patent [19]
Kohler

[11] Patent Number: 5,579,760
[45] Date of Patent: Dec. 3, 1996

[54] PROCESS AND APPARATUS FOR PRODUCING AN AEROSOL FROM A PULVERULENT SUBSTANCE

[75] Inventor: Dieter Kohler, Schmallenberg-Winkhausen, Germany

[73] Assignee: Angiomed AG, Karlsruhe, Germany

[21] Appl. No.: 433,425

[22] PCT Filed: Oct. 30, 1993

[86] PCT No.: PCT/EP93/03033

§ 371 Date: Jul. 10, 1995

§ 102(e) Date: Jul. 10, 1995

[87] PCT Pub. No.: WO94/11043

PCT Pub. Date: May 26, 1994

[30] Foreign Application Priority Data

Nov. 6, 1992 [DE] Germany .................... 42 37 568.1

[51] Int. Cl.⁶ ................................................ A61M 15/00
[52] U.S. Cl. .............................. 128/203.15; 128/200.14; 128/203.12

[58] Field of Search ............... 128/200.14, 203.15, 128/203.12; 604/58

[56] References Cited

U.S. PATENT DOCUMENTS

| | | | |
|---|---|---|---|
| 4,452,239 | 6/1984 | Malem | 128/203.15 |
| 5,161,524 | 11/1992 | Evans | 128/203.15 |
| 5,476,093 | 12/1995 | Lankinen | 128/203.15 |

*Primary Examiner*—Aaron J. Lewis
*Attorney, Agent, or Firm*—Antonelli, Terry, Stout & Kraus

[57] ABSTRACT

A process for producing an aerosol from a pulverulent substance, particularly for inhalation. In a turbulent agitating or whirling chamber, firstly a vacuum is produced, then gas is allowed to flow into the agitating chamber in such a way that the pulverulent substance contained therein is whirled up and an aerosol is produced, and immediately thereafter aerosol is discharged from the aerosol-containing agitating chamber.

22 Claims, 5 Drawing Sheets

PROCESS AND APPARATUS FOR PRODUCING AN AEROSOL FROM A PULVERULENT SUBSTANCE

BACKGROUND OF THE INVENTION

The invention relates to a process and an apparatus for producing an aerosol from a pulverulent substance, particularly a medicinal substance.

For the treatment of diseases of the respiratory tracts, medicinal substances are preferably applied by inhalation, because as a result the active substance is deposited in relatively high concentration on the respiratory tracts, whereas effects due to the distribution of the medicinal substance throughout the body, so-called systemic effects, remain relatively limited. In addition, the inhalation of a medicinal substance is also suitable for systemic therapy.

The production of a suitable aerosol with effectively inhalable, i.e. relatively small, particles in part leads to considerable difficulties, particularly when based on a pulverulent substance. Therefore numerous processes and apparatuses have been developed which in different ways attempt to produce such a readily inhalable aerosol.

Despite the numerous possibilities in connection with inhalators the use of propellants, particularly those prejudicial to the environment, must be avoided. DE-A1-40 27 390 discloses a propellant-free inhalator, in which the medicinal substance is received in powder form in a storage container. By means of a dosing device the substance dose is removed prior to the fitting of a mouthpiece, and from there the patient inhales with the aid of active breathing in, the substance being entrained by the air flow formed as a result of breathing in. In order to obtain inhalable particles of the pulverulent substance, there is an air chamber for distributing the substance in the air flow being formed. The particle size in the case of this inhalator is dependent to a significant extent on the intensity and nature of breathing in, so that adequately small particles of the dosed substance cannot be guaranteed in all cases. For use in the known inhalator the medicinal substance, optionally accompanied by the admixing of adjuvants, is compacted to form a pressed article. Using a moving edge or brush powder is removed from the pressed article and is admixed with the breathing air of the patient. The process is not suitable for mass production, because it is not possible to produce with a homogeneous hardness the pressed articles formed from tile medicinal substance and adjuvant.

DE-A-40 27 391 discloses a further propellant-free inhalator with a similar construction. In order to make the breathed in substance quantity reproducible and simultaneously attain inhalable particles, an air volume stored in a cylinder is automatically released in reaction to the breathing in and is led to a nozzle, so that the dosed substance is blown by the active air flow which forms into the throat of the patient. However, in connection with respiration triggering problems are caused by the considerable effort and expenditure necessary for a precise air volume release triggered by respiration.

However, known processes and apparatuses generally suffer from the disadvantage that there is an imprecise aerosol with respect to the particle spectrum and mist density. Fundamentally, on blowing in, there is a whirling up or turbulent agitation of a considerable air quantity, which is much larger than the blown in volume. This air quantity must normally be trapped in a corresponding container if not inhaled by the patient. If it is directly inhaled by the patient, then the intrabronchial deposition differs to a very marked extent, because as a function of the inhalation flow the particle spectrum is greatly modified mainly by impaction.

On blowing in the accelerated air is decelerated by that which is already present. Therefore the kinetic energy striking the aerosol is not high.

If the blown in aerosol volume is intermediately stored in a container, so that the patient always inhales an identical particle spectrum, large volumes are necessary. In the case of dosing aerosols it is often necessary to use as attached devices spacers having a volume of 300 to 800 ml.

Another inhalator with an active air flow is known from WO-A-90/07351. The air flow is made ready by a pressurized gas source, or is produced with the aid of a piston/cylinder arrangement, and is guided in a nozzle arrangement with a varying cross-section, in order to in planned manner increase the flow rate of the air flow. Close to the maximum flow rate in the nozzle arrangement a duct issues into the flow path and constitutes a connection to a storage container for the pulverulent substance. The substance is sucked in by the active air flow and conveyed into a mixing chamber, where a good distribution of the particles is to take place. In connection with this inhalator it must be borne in mind that the preparation of the aerosol takes place completely independently of the inhalation of the patient, and also an active air flow is directed into the respiratory tracts of the patient, so that a good distribution cannot be expected before and during inhalation.

SUMMARY OF THE INVENTION

The problem solved by the invention is to provide a process and an apparatus for producing an aerosol from a pulverulent substance with which a high density aerosol with inhalable, lung-reaching, and in particular relatively small particles of the substance are made available for inhalation, without having a disturbing influence on the breathing in of the aerosol.

In the case of the invention, the whirling up or turbulent agitation of the pulverulent substance takes place in a clearly defined, closed whirling or agitating chamber by the inflow of a gas, and in particular air. As a result of mechanically producing the vacuum by means of a piston or a pump a much lower pressure can be produced than would be achieved by the suction action of a patient. This permits a much higher inflow speed, which leads to the desired, good atomization of the substance particles. Subsequently the resulting aerosol, preferably also a clearly defined quantity or volume at normal pressure, is introduced into the interior of a mouthpiece in a predetermined quantity, preferably in that there is initially a pressure increase in the whirling or agitating chamber and then by opening an outlet the predetermined aerosol quantity flows out up to pressure balance. Then, after closing the agitating chamber outlet, the patient or user can breath in the aerosol from the mouthpiece.

The invention makes it possible to release and agglomerate a micronized powder in a small volume. The considerable air volume normally obtained on blowing in the powder, and the resulting air excess, which is often a multiple of the blow-in air required, are rendered avoidable by the present invention. Therefore there is no longer any need for large-volume containers. The small volume is very precisely definable and leads to a dosage simplification. A stable aerosol forms, because larger particles are immediately separated by sedimentation. Unusually high powder densities of up to 10 mg/l can be achieved with the aid of the invention, and consequently correspondingly small dosing aerosols are possible. In the process according to the invention the air flows in a clearly defined volume. Therefore the inflowing air always fills the same volume. It leads to the deagglomeration and comminution of the powder in an extremely high concentration. However, as stated hereinbefore, on blowing in a powder to bring it into an aerosol form, the turbulent agitation volume thins or rarefies the aerosol. In the case of the process according to the invention there is such a high aerosol density that the limit concentration which can be carried by the air is reached. Thus, particularly the coarser particles are rapidly deposited within seconds and this leads to a stable mist or aerosol density with a roughly identical particle spectrum. Such a high mist density cannot be achieved by blowing in. The mist density is independent of the filling quantity as a result of the "supersaturation" of the air by the aerosol. This is not the case in known processes. This in itself sets aside the process and apparatus according to the invention from the prior art. The small volume also has the important advantage of handiness.

According to preferred developments, prior to the inflow of a gas into the whirling or turbulent agitation chamber, a pressure is produced therein of below 100 Pa, such as approximately 70 Pa, preferably below 50 Pa, e.g. 30 Pa and advantageously this is achieved in that the agitation chamber can be enlarged in the closed state for producing a vacuum therein, and that after opening the outlet the gas flows into the said chamber as a result of the vacuum produced therein. This permits flow rates in the agitating chamber of above 200 m/sec, which lead to the desired deagglomeration by overcoming the adhesion of the particles. This produces a lung-reaching particle fraction of 90% and higher.

In the case of a vacuum the air flows in unhindered manner onto the pulverulent substance. The speed is only limited by the inertia of the air and the level of the vacuum. There is a very high mist density production.

According to preferred developments the vacuum in the agitating chamber containing the substance is produced by increasing the size of said chamber and the aerosol is discharged from the chamber containing the same by pressing out, and in particular the gas flowing into the agitating chamber is ambient air.

According to further preferred developments a mouthpiece connectable to the agitating chamber can be sealed off with respect to the environment during the forcing of the aerosol into the mouthpiece and optionally up to an outlet of said mouthpiece for the subsequent breathing in by the patient and/or a mouthpiece connectable with the agitating chamber, following the forcing in of the aerosol into the mouthpiece, is open to the environment even when the user's mouth is attached thereto.

Whilst a turbulent air flow is produced for whirling purposes and is also desired for this purpose, the air in and through the mouth of the patient and his trachea and into the lung must flow in as laminar a way as possible. According to a preferred development, the aerosol flows in substantially laminar form into the mouthpiece, this being achieved in that between the outlet of the agitating chamber and the interior of the mouthpiece, a flow straightener is provided. The latter is in particular constructed as a perforated plate.

According to further preferred developments of the invention, the agitating chamber is constructed in the storage chamber for the substance. In addition, between the inner area of a mouthpiece and the environment a closable opening is provided, when it opens the agitating chamber outlet for the outflow of the aerosol from said chamber 18 closed and/or between the interior of a mouthpiece and the environment is provided a closable opening, which is opened on closing the agitating chamber outlet. Whilst the opening to the interior of the mouthpiece on the one hand and the agitating chamber outlet on the other can be independently controlled in a suitable manner, according to a preferred development a closing member for the agitating chamber outlet and a closing part for the opening between the interior of the mouthpiece and the environment are interconnected, and in particular the closing member and closing part are rigidly interconnected.

In order on the one hand to obtain an opening of the inlet and outlet with respect to the turbulent agitating chamber after producing a vacuum and without additional actuating processes, and on the other to obtain an outflow of the gas after opening the outlet with a predetermined volume by prior building up of an overpressure, according to further developments the closing part for the agitating chamber outlet is connected to a piston movable therein by means of a thread, and a piston varying the agitating chamber volume is connected to a tappet or push rod for closing the outlet cooperating with a closing member of an outlet of the agitating chamber.

In order that the movements of the piston in the cylinder are not impeded by powder adhering to the inside of the cylinder wall, according to a preferred development the pulverulent substance and the agitating chamber are surrounded by a flexible jacket positioned in the interior of the cylinder, which is fixed on the one hand to the piston and on the other to the cylinder, close to its end remote from the piston, i.e. close to the inlet and outlet.

According to a further development, with the closing member associated a stripping ring fixed to the cylinder.

As in the case of the apparatus according to the invention a predetermined substance is present, only a given number of aerosole can be produced. In order to make it possible to detect the emptying of the cylinder, a counter or meter is provided. According to a preferred development, is formed by the fact that on an operating rod of the piston in the cylinder is provided a flexible nose, which acts on a small gear or a pinion, which by means of a worm constructed on one end face drives a larger gear, which is provided with colour markings, which can be observed through a window. In place of the gear it is also possible to provide a toothed belt provided with corresponding markings.

According to another preferred development, an opening leading into the turbulent agitating chamber is formed in the piston, the latter being rigidly connected to an outer, cylindrical casing by means of a piston rod end a web arranged transversely in the casing and the cylinder is formed by a cylindrical cylinder body with an internal diameter adapted to the piston, and the cylinder is displaceable in the casing in such a way that the agitating chamber can be enlarged. According to a further development, a closing part is provided, which is fitted to one arm of a two-armed lever mounted on the piston rod, the cylinder body having a nose which cooperates with another arm of the lever, so that on reaching the position of the cylinder body in which the agitating chamber is at its largest, the opening in the piston is freed.

According to a further preferred development, the agitating chamber is formed by a bellows, which is closed by cover plates at its end faces, and in one cover plate is provided a first valve mechanism for the flow of gas which flows into the evacuated agitating chamber and which is released by a release mechanism when the agitating chamber is at its largest through the expansion of the bellows, and in particular a second valve mechanism is provided through which the gas present in the agitating chamber on compressing the bellows can escape therefrom. There is optionally a third valve means which is also released by the release mechanism if, as a result of the expansion of the bellows, the agitating chamber is in its largest state, and through which the aerosol produced in said chamber can be discharged. It is also possible to provide a breathing tube, to which is connected the first and third valve means and which has a constriction in the area between the two connecting points of the valve mechanisms through which the flow rate of the air flow on breathing through the breathing tube is increased.

The invention provides a process and an apparatus in which the aerosol has a high, inhalable active substance proportion in the case of a good dosing constancy. It has been found that the inhalable active substance percentage is 90%, whereas it only 20% in the prior art. Thus, the efficiency is greatly increased by the invention, and much less active substance can be used because it is better utilized. The quantity variation was much less than in the case of known processes and apparatuses, namely only 11%, whereas the variation coefficient in the known processes and apparatuses is a multiple thereof Moreover, as stated, compared with the prior art there is a relatively narrow particle size distribution of approximately 0.6 to just below 6 μm, whereas larger particles virtually do not occur in the aerosol.

The process according to the invention and embodiments of the apparatus according to the invention are described in greater detail hereinafter relative to the attached drawings, wherein;

DETAILED DESCRIPTION OF PREFERRED EMBODIMENTS

The process according to the invention will firstly be explained by means of a first embodiment of the apparatus according to the invention and relative to FIG. 1. These and further embodiments of the apparatus will be described in greater detail hereinafter.

Figure 1A:
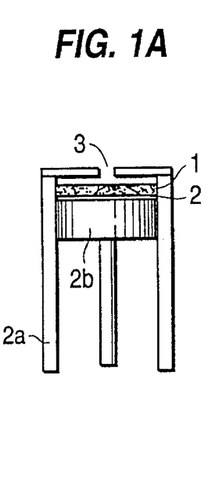
FIGS. 1A to 1D illustrate a first embodiment of the apparatus according to the invention and the individual steps of the process according to the invention.

FIG. 1A illustrates the first stage of the process, according to which a clearly defined quantity of pulverulent substance 1 is brought into a closed whirling or turbulent agitating chamber 2. In the first embodiment the closed agitating chamber 2 is the interior of a cylinder 2a of a piston-cylinder arrangement. The substance can be introduced e.g. by an opening 3 provided in the cylinder, but also by a specially provided opening or in some other way; for example the piston 2b can be drawn out of the cylinder 2a, the substance introduced, and then the piston reinserted in the cylinder.

Figure 1B:
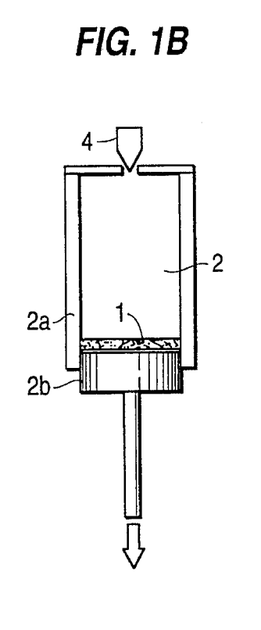

FIG. 1B illustrates the second stage of the process according to the invention, in which a clearly defined vacuum is produced in the substance-containing agitating chamber 2. In the case of a piston-cylinder arrangement, said vacuum is obtained in simple manner in that the piston 2b is brought from the advanced position shown in FIG. 1A to the retracted position shown in FIG. 1B. The opening 3 of the cylinder 2a is closed with u suitable closing member 4. On producing the vacuum in the interior of the substance-containing agitating chamber 2 the pulverulent substance 1 remains substantially uninfluenced, as can be gathered from FIGS. 1A and 1B by the substance 1 in the vicinity of the piston 2b.

Figure 1C:
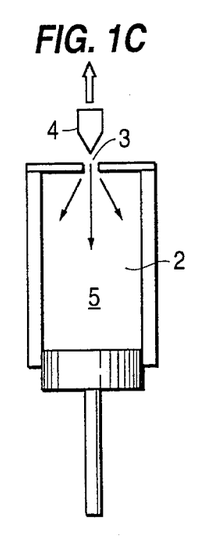

The third stage of the process according to the invention illustrated in FIG. 1C. According to this, a gas, and preferably ambient air, is allowed to flow rapidly, but in controlled manner, into the substance-containing agitating chamber 2. Thus, an air flow is produced which flows in rapid, but controlled, manner into the agitating chamber. In the represented embodiment, this takes place by opening the closing member 4 of the opening 3. The resulting air flow is indicated by the arrows in FIG. 1C. It whirls up the pulverulent substance and ensures a good distribution of the particles in the available agitating chamber 2 so that the desired aerosol 5 is produced and almost completely fills the agitating chamber. The particle distribution is brought about under very precisely definable conditions because as a result of the size and design of the available agitating chamber 2 and the opening 3 through which the air flow passes into said chamber, as well as through the position thereof, the flow behaviour and consequently the turbulent agitation of the pulverulent substance can be determined to a significant extent.

Thus, it is e.g. possible to control in planned manner the agglomeration and sedimentation of larger particles which are less suitable or even unsuitable for inhalation. This assists the formation of a homogeneous aerosol with a constant density.

Figure 1D:
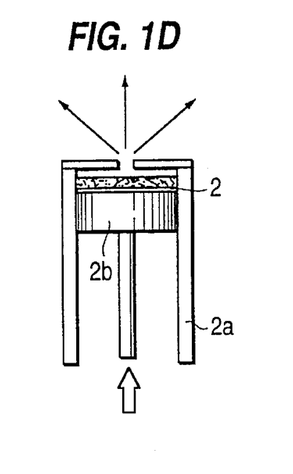

In the fourth stage of the process according to the invention and as illustrated in FIG. 1D, the aerosol 5 that has been produced is discharged from the agitating chamber 2 and is made available for inhalation by the patient. In the first embodiment the aerosol is discharged by simply forcing it out, in that the piston 2b is returned to its advanced position. However, discharge can also take place in that during breathing in the patient sucks the aerosol produced from the agitating chamber. However, in all cases aerosol discharge takes place in such a way that a disturbing influencing of the inhalation process on breathing in is avoided, because no whirling up is produced in planned form during this stage. The aerosol 5 with a good particle distribution is available prior to discharge in the agitating chamber 2, which it uniformly fills. Therefore the discharge can be completely based on the conditions to be taken into consideration with respect to the inhalation. In particular, it is possible to avoid a disturbing influence on the breathing in by an excessive or forced air flow.

In order to bring about an optimum adaptation of the openings, to their particular task, separate openings can be provided for the inflow of air into the evacuated agitating chamber and for the forcing out of the aerosol, as well as for introducing the substance into said chamber.

The construction of the first embodiment of the apparatus according to the invention is apparent from the above description of the inventive process by means of said embodiment.

Thus, the first embodiment of the apparatus comprises an arrangement constituted by a cylinder 2a and a piston 2b, which together define a whirling or turbulent agitating chamber 2. The piston 2b is movably arranged in the cylinder 2a and can be moved backwards and forwards between an advanced and a retracted position. The size of the agitating chamber can consequently be determined by means of the piston position. The agitating chamber 2 has an opening 3 through which the dosed substance 1 is brought into said chamber 2, through which a gas, preferably ambient air, which turbulently agitates the substance flows in, and through which the produced aerosol 5 produced is discharged. In order that the agitating chamber 2 is closed during the production of the defined vacuum, a closing member 4 is provided.

So as to prevent any impairing of the mobility of the piston 2b in the cylinder 2a, in the interior of the latter can be provided an additional flexible container, such as a bellows or a thin-walled plastic hose for the reception of the substance. On enlarging the agitating chamber, i.e. on moving the piston 2b to the retracted position, there is also an enlarging of the flexible chamber as a result of the externally applied vacuum. Preferably the flexible container is also fixed to the piston, so that it moves with the latter.

Figure 2:
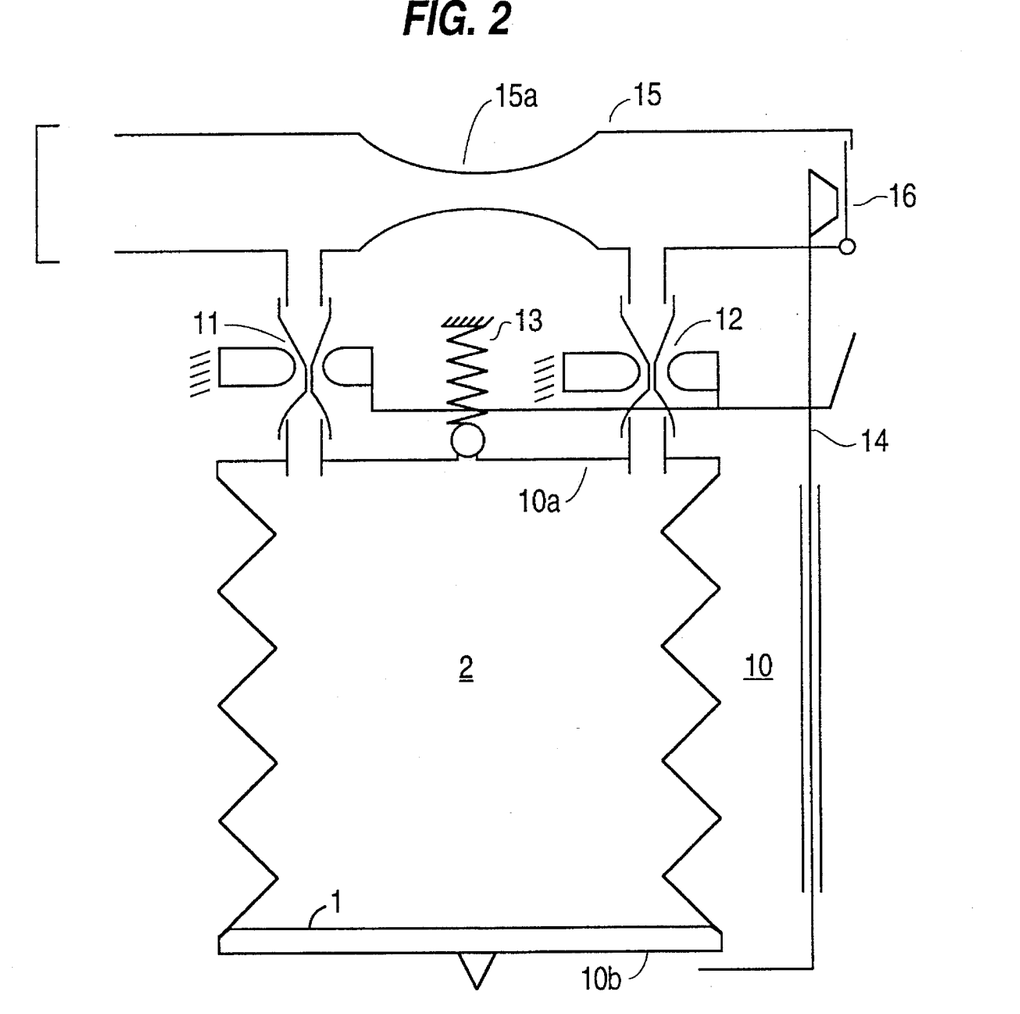
FIG. 2 illustrate a second embodiment of the apparatus according to the invention.

FIG. 2 shows a second embodiment of the apparatus according to the invention, where a bellows 10 is used as the component defining the agitating chamber. The bellows 10 is closed at its end faces by means of cover plates 10a, 10b. In the cover plate 10a there are three valves 11, 12 and 13, whereof the constructionally identical valves 11 and 12 are used for the inflow of air into the evacuated agitating chamber 2 and for the discharge of the aerosol therefrom, whilst the valve 13 allows an escape of air on compressing the bellows 10. After again enlarging the bellows 10 in order to produce a vacuum in the substance-containing agitating chamber 2, a slide 16 is operated as the release mechanism for the valves 11 and 12, and as a result said two valves are opened, being represented in FIG. 2 as hose valves.

By means of the two valves 11 and 12 the bellows 10, and therefore the agitating chamber 2, is connected in shunt manner to a breathing tube 15 through which the patient breaths in and which for this purpose is provided at one end with a mouthpiece for the patient. At this end of the breathing tube 15 is provided further valve 16, which prevents a blowing into the breathing tube. The breathing tube 15 has a constriction 15a, so that as a result of the pressure drop an adequate air flow flows through the agitating chamber 2. Devices preventing the substance 1, particularly a pulverulent substance, passing into the valves and therefore impairing the operation of the valves or the oral ingestion of the substance 1 by means of the breathing tube 15 are not shown.

Figure 3A:
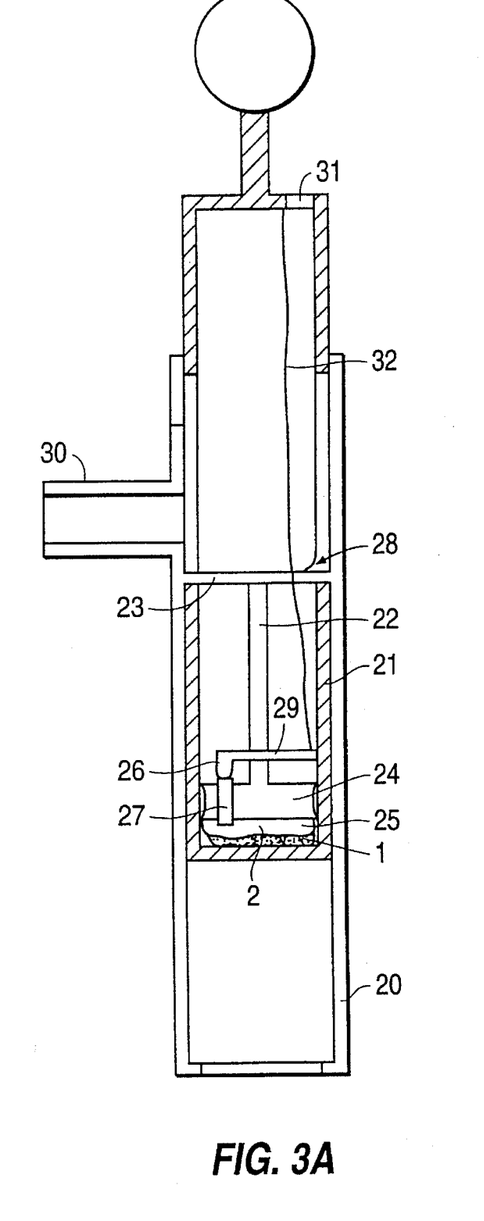
FIGS. 3A and 3B illustrate a third embodiment of the apparatus according to the invention.
Figure 3B:
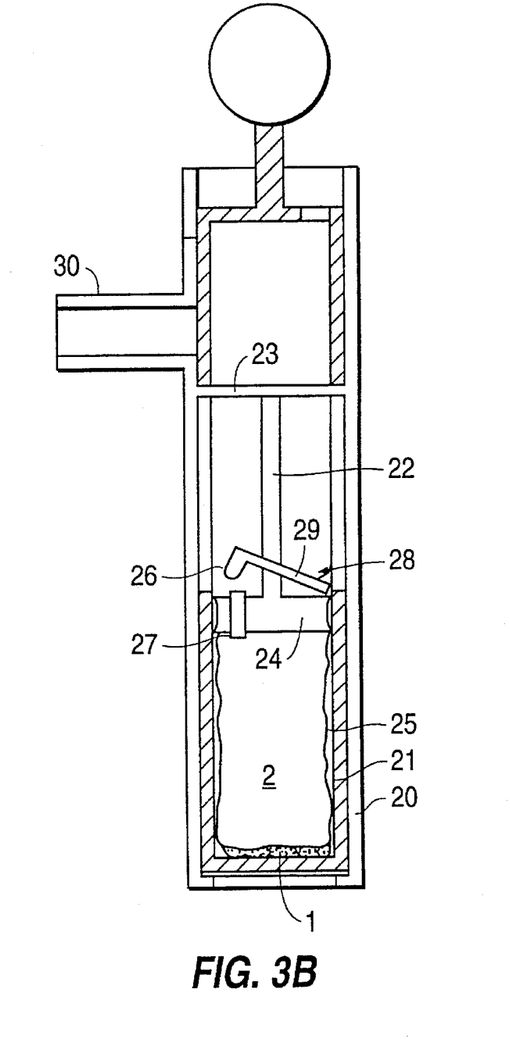

A third embodiment of the apparatus according to the invention is shown in FIGS. 3A and 3B. The apparatus comprises an outer cylindrical casing 20 and an inner cylindrical cylinder body 21, which is movable in the casing between two positions as shown in FIGS. 3A and 3B. In the interior of the casing one end of a piston rod 22 is rigidly connected to the casing 20 by means of a web 23 running transversely through said casing. At its other end the piston rod carries a piston 24, which is adapted to the internal diameter of the cylinder body 21 and defines with the latter the agitating chamber 2. If the cylinder 21 is moved, the piston 24 slides on the inner wall of the cylinder body. In the thus defined agitating chamber 2 is provided an additional flexible plastic container 25 connected in gas-tight manner to the piston 24.

In the construction shown in FIG. 3A the turbulent agitating or whirling chamber 2 has the smallest volume. The pulverulent substance 1 is located in the flexible plastic container 25. From this starting position, the cylinder body 21 is moved into the position shown in FIG. 3B. During the movement a plug or stopper 26 closes an opening 27 in the piston, so that as a result of the volume increase in that agitating chamber 2, a vacuum forms and expands the flexible plastic container 25. On reaching the position shown in FIG. 3B, a nose 28 fitted to the inner wall of the cylinder body engages with an arm of a two-arm lever 29 on whose other arm is located the plus 26 closing the opening. Thus, the opening 27 in the piston is freed, so that air flows into the evacuated agitating chamber, the substance is agitated, and the aerosol produced.

The inner cylinder 21 is then drawn upwards again, and the aerosol is forced out of the agitating chamber through the opening 27 into the interior of the cylinder. On the outer casing is fitted a mouthpiece 30 through which the patient can suck the aerosol produced from the space within the cylinder 21. For this purpose the cylinder 21 is hollow and is provided at a suitable point with a passage opening for the sucked-in aerosol. The cylinder body also has an air inlet 31 through which the ambient air on inhaling passes into the interior of the cylinder body. The air flow in through the air inlet moves the aerosol with the whirled-up substance out of the cylinder body, so that the substance is completely inhaled.

Figure 4A:
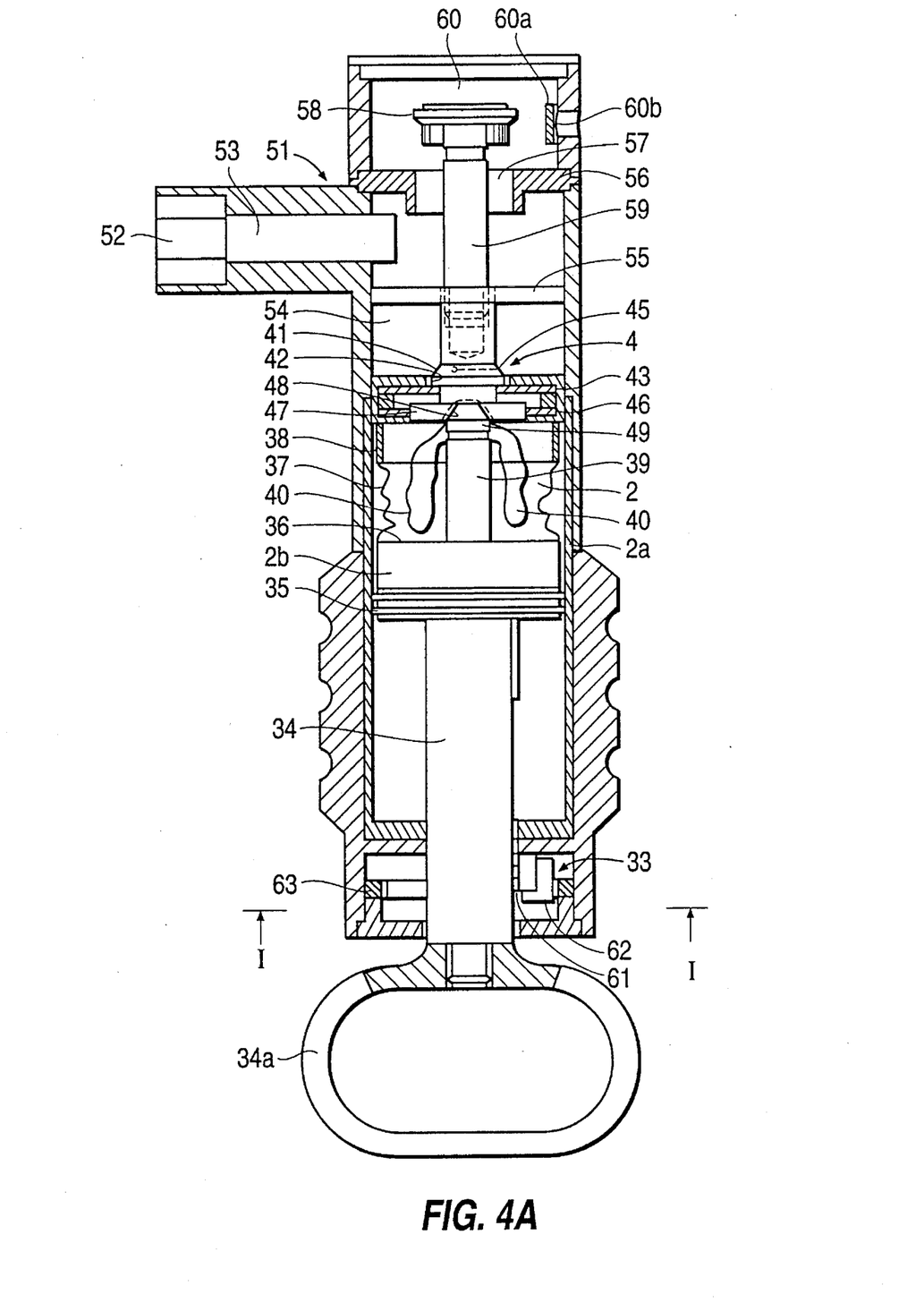
FIG. 4A is a longitudinal sectional view through another preferred embodiment of the apparatus according to the invention with the valve closed.
Figure 4B:
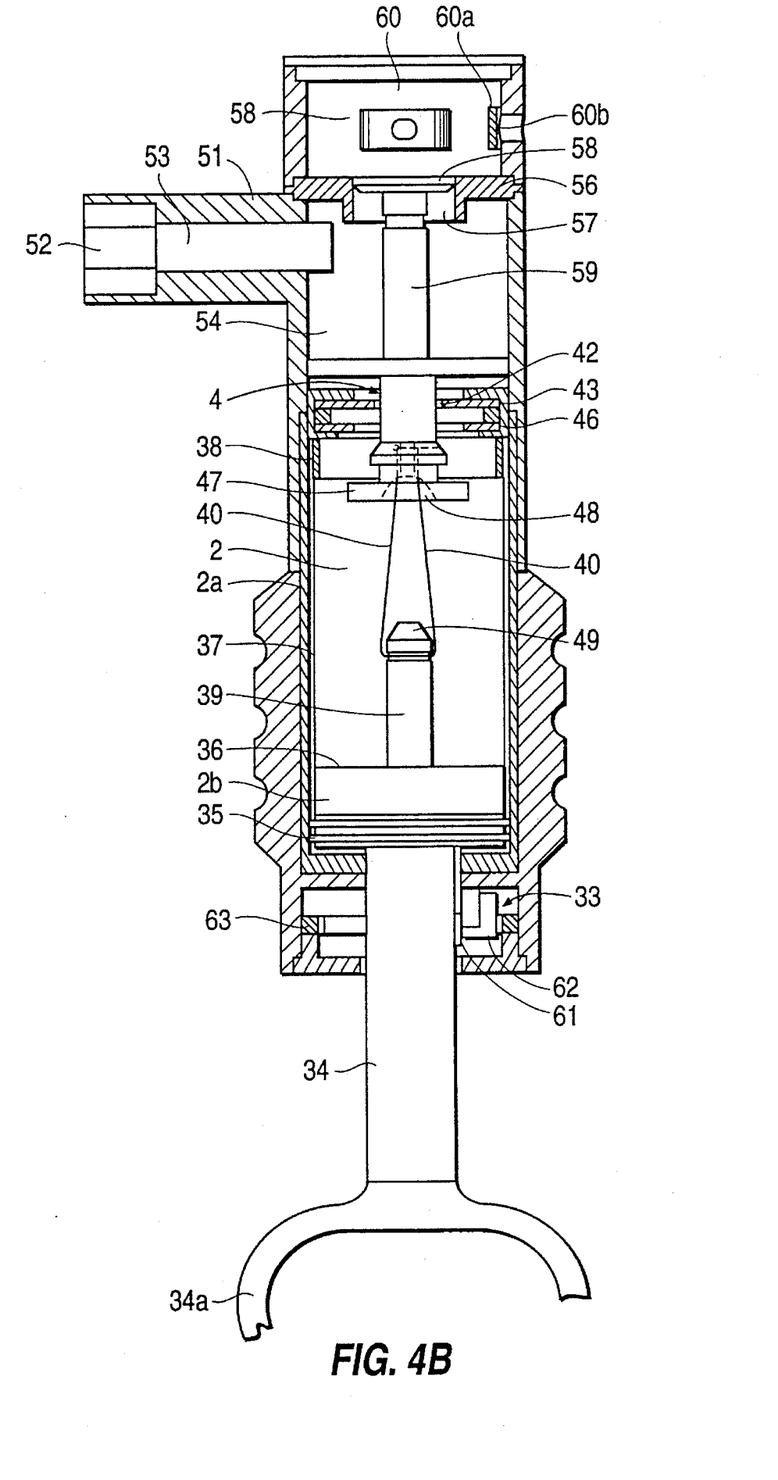
FIG. 4B is a longitudinal sectional view through the apparatus of FIG. 4A with the valve open.
Figure 4C:
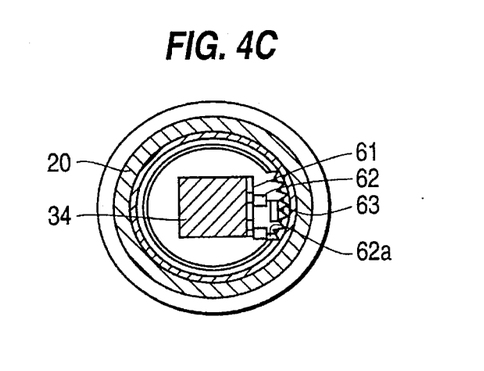
FIG. 4C is a sectional view taken section through the counter along line I—I in FIG. 4A.

The plug-carrying two-arm lever 29 is either pretensioned in such a way that the plus 26 closes the opening 27 in the piston in its inoperative position and only as a result of the action of the nose 28 in the interior of the cylinder body 21 or as a result of the internal pressure of the agitating chamber 2 on moving back the cylinder body 21 into its starting position frees the opening 27, or it is brought with the aid of a thread 32 into the closing position just before the starting position is reached. FIGS. 4A to 4C show an extremely preferred development of an apparatus according to the invention for producing an aerosol and for performing the process according to the invention. The same parts are given the same reference numerals as in the preceding drawings.

In a cylinder 2a the apparatus has a whirling or turbulent agitating chamber 2, in which is also housed all the substance to be agitated. The volume change of the agitating chamber 2 is brought about by a piston 2b, which is displaceable in the cylinder 2a. On the side of the agitating chamber opposite to the piston 2b is provided a closing member 4 in the form of a valve. The piston 2b is displaceable by means of a piston rod 34 projecting from the cylinder 2a, using a grip or handle 34a connected thereto.

The piston is provided with packings 35. With its end face 36 extending to the agitating chamber 2, a flexible sleeve 37 in the form of a latex diaphragm or the like is connected, in much the same way as in the construction of FIGS. 3A and 3B, and is fixed to the wall of the cylinder 2a at 38 in the vicinity of the closing member 4. The agitating chamber 2 is constructed within the sleeve 37, the substance 1 also being located in said sleeve. This ensures that the material does not stick to the inner wall of the cylinder 2a and impede the movement of the piston 2b.

A push rod 39, whose function will be explained hereinafter, projects from the end face 36 of the piston 2b, facing the agitating chamber 2 and into the latter. The closing member 4 has a movable valve body 41 and a valve seat 42. The valve seat 42 formed by a sealing ring 43, which tightly engages on the valve body 41 in the closed state. On the side remote from the agitating chamber 2, the valve body 41 is provided with a conical face 45 which slides along the sealing ring 43 on again moving the valve of the closing member 4. The inside of the sealing ring is preferably cutting edge-like or rounded, and not cylindrical.

Spaced from the sealing ring 43 in the direction of the agitating chamber 2, an elastic stripping ring 46 is fixed to the cylinder 2a and cooperates with a flat cylinder 47 which has a larger diameter than the valve body and which is connected to the latter with respect to the chamber 2. The valve body 41 and cylinder body 47 can be constructed in one piece.

In the cylinder body 47 is formed a centrosymmetrical, frustum-shaped recess 48, which cooperates with a frustum-shaped, front end 49 of the push rod 39 in a manner to be described hereinafter.

To the cylinder 2a is connected a mouthpiece 51, whose main extension direction is at right angles to that of the cylinder 2a. The mouthpiece has an outlet channel 53 leading to an outlet 52.

A perforated plate 55 is positioned between the outlet area 54 of the agitating chamber 2 behind the closing member 4 end the outlet channel 53 through which the aerosol forced out of the chamber 2, can be forced out of the opening 52, the aerosol flow being straightened, i.e. brought into a substantially laminar flow and aerosol turbulence caused by the whirling up in the agitating chamber 2 is substantially suppressed.

In a partition 56 of the mouthpiece 51, remote from the closing member 4 and preferably aligned with the latter, is formed an opening 57 which can be closed by a closing plate 58 which is closable by means of an axial attachment 59 of the valve body 41 on opening the latter and is opened when the valve body 41 is closed.

The opening 57 issues into an intermediate space 60, which is connected with the environment by openings 60b in the cylinder wall 2a on its inside coverable by flaps 60 a acting as check valves. Thus, by means of the openings 60b and the openings 57, air can be sucked In, but not forced out.

As stated, at the end of the cylinder 2a remote from the mouthpiece 51 is provided a counter 33. For this purpose on the piston rod 34 is formed a resilient nose 61 which acts on a pinion 62 whose axis is oriented perpendicular to the axis of the piston rod 34. On the remote end face of the pinion 62 is constructed a worm 62a which engages in a large gear rim 63 with internal teeth. The axis of gear rim 63 parallel to the axis of the piston rod 34, and optionally coincides therewith. On the outside of the gear rim 63 are provided markings which can be seen through a window.

Alternatively it would be possible to provide a toothed belt, operable in the same way by means of a resilient attachment on the piston rod 34 and having colour markings visible through a window. Thus, it is possible in both cases to establish whether the intended number of operations has been performed and therefore whether the substance originally introduced into the apparatus has been used up.

The apparatus according to this development of the invention functions as follows. The piston 2b is advanced from the position shown in FIG. 4A, where at its highest it projects so far upwards, i.e. towards the mouthpiece 51, that the tip 49 of the attachment 39 projects into the conical recess 48 of the plate 47 and is drawn downwards by means of the handle 33, i.e. from the mouthpiece 51. The closing member 4 is closed. As a result the agitating chamber 2 is provided with a vacuum.

Shortly before the piston 2b reaches the end face of the cylinder 2a remote from the mouthpieces 51, the tension-proof thread 40, which is also relatively inelastic with respect to tension and which is fixed between the valve body 41 and the extension or attachment 39 of the piston 2b, is in its tensioned position. A further drawing down of the piston 2b to the end face remote from the mouthpiece 51 ensures that the closing member 4 is opened by the drawing down of the valve body 41 (FIG. 4B). Simultaneously the opening 47 is closed by the closing plate 58.

Through the opened closing member 4, by means of the opening 52 of the mouthpiece, air can flow into the agitating chamber 2 as a result of its vacuum, so that the substance 1 therein is whirled up, and consequently an aerosol is formed.

Subsequently, by means of the handle 33, the piston 2b is again forced onto the mouthpiece 51. The aerosol formed in the agitating chamber 2 is initially forced out of the same and pressed through the perforated plate 55 into the channel 53 of the mouthpiece 51 until the front tip 49 of the piston extension 39 engages in the recess 48 of the plate 47 of the closing member 4 and again closes the latter. Simultaneously the opening 57 is opened, in that the closing plate 58 is raised from it.

For so long as the opening 57 is closed and therefore the closing member 4 opened, the user is unable to breath in from the apparatus according to the invention. This prevents an undefined aerosol quantity being sucked by breathing in from the agitating chamber 2. Thus, during the forcing out of aerosol from the agitating chamber 2 and the opening time of the closing member 4, the opening 57 is closed, so that a precisely defined aerosol quantity is brought from the chamber 2 into the mouthpiece 51 as is determined by the stroke of the piston 2b. If during this time the opening 57 were opened, then counterflow air could flow in through the opening 57 and the opened closing member 4 into the agitating chamber 2, so that as a result of breathing in the user could suck in a non-defined aerosol quantity from the agitating chamber 2.

After opening the opening 57, the user can inhale the aerosol in the channel 53 of the mouthpiece 51. Air can subsequently flow via the opening 60b, the space 60 and the opening 57, because during suction the flaps 60a are raised from the opening 60b to free the latter (FIG. 4A). Subsequently the apparatus according to the invention is ready for reuse.

What is claimed is:

1. A process for producing an aerosol, comprising the steps of:

(a) inserting a precisely defined quantity of a pulverulent substance into a chamber having a predetermined volume;

(b) evacuating the chamber with the pulverulent substance therein to produce at least a partial vacuum in the chamber;

(c) allowing a gas to flow into the evacuated chamber to cause the pulverulent substance therein to whirl up and form an aerosol; and (d) immediately after step (c), forcing a predetermined volume of the aerosol from the chamber.

2. A process according to claim 1, wherein step (b) comprises reducing the pressure within the chamber to a pressure of not more than 100 Pa.

3. A process according to claim 1, wherein step (b) comprises increasing the size of the chamber.

4. A process according to claim 1, wherein step (b) comprises reducing the pressure within the chamber by means of suction.

5. A process according to claim 4, wherein step (b) comprises activating a motor-driven pump to reduce the pressure within the chamber.

6. A process according to one of the claims 1 and 2 to 4, wherein step (d) comprises forcing the aerosol out of the chamber.

7. A process according to claim 1, wherein the chamber includes a mouthpiece, and step (d) comprises sealing off the mouthpiece with respect to the environment, and forcing the aerosol into the mouthpiece.

8. A process according to claim 1, wherein the chamber includes a mouthpiece, and step (d) comprises forcing the aerosol into the mouthpiece, and then opening the mouthpiece to the environment.

9. A process according to claim 1, wherein step (d) comprises causing the aerosol to flow in a substantially laminar manner.

10. A process according to claim 1, wherein step (b) comprises reducing the pressure within the chamber to a pressure of not more than 50 Pa.

11. An apparatus for producing an aerosol from a pulverulent substance, said apparatus comprising:

a storage chamber having a predetermined volume, with at least one opening thereinto, and having therein a precisely defined quantity of the pulverulent substance;

first openable closing means for closing the at least one opening of the storage chamber;

means for producing a vacuum in the storage chamber, thereby generating an evacuated storage chamber;

means for introducing a gas through the at least one opening into the evacuated storage chamber to cause the pulverulent substance therein to whirl up and form an aerosol; and means for forcing a predetermined volume of the aerosol through the at least one opening from the storage chamber.

12. An apparatus according to claim 11, wherein the means for producing the vacuum comprises a pump connected to the at least one opening.

13. An apparatus according to claim 11, wherein the means for producing a vacuum comprises means for enlarging the volume of the chamber while the closing means is closing the at least one opening.

14. An apparatus according to claim 13, wherein the means for introducing a gas comprises means responsive to opening of the first closing means to permit the gas to flow into the storage chamber as a result of the vacuum therein.

15. An apparatus according to one of the claims 13 and 14, wherein the storage chamber comprises a cylinder, and the vacuum producing means comprises a piston within the cylinder permitting enlargement of the storage chamber by the displacement of the piston with respect to the cylinder.

16. An apparatus according to claim 15, wherein:

the at least one opening of the storage chamber passes through the cylinder, and the first closing means comprises a closure member for closing the at least one opening of the storage chamber, and a thread connecting said closure member to said piston to pull said closure member from the at least one opening as said piston moves, opening the at least one opening.

17. An apparatus according to claim 15, wherein:

the at least one opening of said storage chamber passes through said cylinder, and said first closing means comprises a closure member for closing the at least one opening of said storage chamber, and a push rod connecting said closure member to said piston to push said closure member from the at least one opening as said piston moves, opening the at least one opening.

18. An apparatus according to one of the claim 11, wherein:

the storage chamber includes an agitating chamber having an outlet, second openable closing means for closing the agitating chamber outlet, a mouthpiece having a first end communicating with the agitating chamber outlet and a second end, a first opening communicating with the mouthpiece first end and the agitating chamber outlet, and a second opening communicating with the mouthpiece second end for removal of the precisely defined volume of the aerosol therethrough; and the first closing means includes means responsive to opening of the agitating chamber outlet for closing the storage chamber first opening.

19. An apparatus according to claim 18, wherein said responsive means is further responsive to closing of the agitating chamber outlet, for opening the storage chamber first opening.

20. An apparatus according to claim 19, wherein said responsive means includes connecting means interconnecting the first closing means and the second closing means.

21. An apparatus according to claim 20, wherein said connecting means is a rigid connecting means.

22. An apparatus according to claim 11, further comprising a flow straightener connected to the storage chamber outlet, and a mouthpiece connected to the flow straightener for removal therethrough of the aerosol in a laminar flow.

* * * * *